(12) United States Patent
Qi et al.

(10) Patent No.: US 11,744,737 B2
(45) Date of Patent: Sep. 5, 2023

(54) SKIN AUDIBLE WATCH FOR ORIENTATION IDENTIFICATION AND AN ORIENTATION IDENTIFICATION METHOD

(71) Applicants: Yong Qi, Xi'an (CN); Hongyan Chen, Xi'an (CN); Linshan Yan, Xi'an (CN); Ningzhan Zhang, Xi'an (CN)

(72) Inventors: Yong Qi, Xi'an (CN); Hongyan Chen, Xi'an (CN); Linshan Yan, Xi'an (CN); Ningzhan Zhang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 27 days.

(21) Appl. No.: 17/554,707

(22) Filed: Dec. 17, 2021

(65) Prior Publication Data
US 2022/0378618 A1     Dec. 1, 2022

(30) Foreign Application Priority Data

May 25, 2021   (CN) .......................... 202110571833.3
May 25, 2021   (CN) .......................... 202121131338.2

(51) Int. Cl.
| | |
|---|---|
| H04R 1/20 | (2006.01) |
| H04R 3/00 | (2006.01) |
| G04G 21/00 | (2010.01) |
| A61F 11/04 | (2006.01) |
| G04G 21/06 | (2010.01) |

(Continued)

(52) U.S. Cl.
CPC ............ *A61F 11/045* (2013.01); *G04G 21/06* (2013.01); *G09B 21/009* (2013.01); *H04R 1/326* (2013.01); *H04R 3/005* (2013.01)

(58) Field of Classification Search
CPC . H04R 1/20; H04R 1/22; H04R 1/222; H04R 1/32; H04R 1/326; H04R 1/40; H04R 1/406; H04R 3/00; H04R 3/005; H04R 2201/40; H04R 2430/20; H04R 2430/21; G09B 21/009
See application file for complete search history.

(56) References Cited

U.S. PATENT DOCUMENTS

| | | | |
|---|---|---|---|
| 5,337,364 A * | 8/1994 | Fitch ..................... | A61F 11/04 340/407.1 |
| 10,261,474 B2 * | 4/2019 | Han ..................... | G06F 3/04842 |
| 10,610,111 B1 * | 4/2020 | Tran ..................... | A61B 5/411 |

(Continued)

*Primary Examiner* — Thang V Tran

(57) ABSTRACT

A skin audible watch for orientation identification includes a dial (1) and a strap (2). A plurality of sound collection modules (3) are arranged along a circumference of the dial (1), and the sound collection modules (3) are sequentially connected with a digital filter (4), an analog-to-digital converter (5), a single-chip microcomputer (6), and a row and column drive module (7); the single-chip microcomputer (6) is also connected with vibration motors (8) and a gyroscope (9); a number of the vibration motors corresponds to a number of orientations; the digital filter (4), analog-to-digital converter, single-chip microcomputer, row and column drive module, the vibration motors and the gyroscope are located inside the dial; the row and column drive module is connected with a current contact pin (12), and a free end of the current contact pin extends out of a surface of the vibration motors.

5 Claims, 5 Drawing Sheets

(51) Int. Cl.
H04R 1/32 (2006.01)
G09B 21/00 (2006.01)

(56) References Cited

U.S. PATENT DOCUMENTS

| | | | |
|---|---|---|---|
| 10,613,485 B2* | 4/2020 | Rothkopf | A61B 5/0261 |
| 10,629,226 B1* | 4/2020 | Tong | G10L 15/08 |
| 2011/0157143 A1* | 6/2011 | Choi | G09G 3/3233 |
| | | | 345/212 |
| 2015/0099941 A1* | 4/2015 | Tran | A61B 5/1112 |
| | | | 600/300 |
| 2018/0184920 A1* | 7/2018 | Rabinovich | A61B 5/681 |
| 2020/0367816 A1* | 11/2020 | Panneer Selvam | A61B 5/7475 |
| 2021/0052221 A1* | 2/2021 | Panneer Selvam | A61B 5/1117 |
| 2021/0169417 A1* | 6/2021 | Burton | A61B 5/4857 |
| 2021/0210114 A1* | 7/2021 | Ang | G06F 3/165 |
| 2022/0365564 A1* | 11/2022 | Hui | G06F 1/1656 |

* cited by examiner sequentially connected with a digital filter (4), an analog-to-digital converter (5), a single-chip microcomputer (6), and a row and column drive module (7); the single-chip microcomputer (6) is also connected with vibration motors (8) and a gyroscope (9); a number of the vibration motors (8) corresponds to a number of orientations; the digital filter (4), analog-to-digital converter (5), single-chip microcomputer (6), row and column drive module (7), the vibration motors (8) and the gyroscope (9) are located inside the dial (1); the row and column drive module (7) is connected with a current contact pin (12), and a free end of the current contact pin (12) extends out of a surface of the vibration motors (8).

SKIN AUDIBLE WATCH FOR ORIENTATION IDENTIFICATION AND AN ORIENTATION IDENTIFICATION METHOD

The present application claims priority to Chinese Patent Application No. 202110571833.3, filed on May 25, 2021, which is incorporated by reference for all purposes as if fully set forth herein.

TECHNICAL FIELD

The present invention relates to the technical field of skin audible devices, specifically, a skin audible watch used for orientation recognition, and an orientation identification method using the skin audible watch.

BACKGROUND TECHNIQUE

The World Health Organization estimates that approximately 466 million people worldwide suffer from disability hearing loss, and by 2050, more than 900 million people will suffer from hearing loss. China has the largest number of hearing disabilities in the world. There are about 27.8 million hearing disabilities, accounting for more than 30% of the disabled in the country. In life, most hearing impaired people use medication, surgical implantation of cochlear implants, and wearing hearing aids to obtain certain rehabilitation effects, but these methods have certain limitations for people with limited resources. Skin audible or skin hearing is a new technology to solve the hearing problem of deaf patients. By stimulating the human skin, the sound signal is transmitted to the cerebral cortex, so that the hearing impaired can perceive the sound. Existing skin audible devices cannot distinguish the location of the sound source.

SUMMARY OF THE INVENTION

The purpose of the present invention is to provide a skin audible watch based on orientation (position) recognition, which solves the problem that the skin audible device in the prior art cannot distinguish the sound source position.

In one embodiment, the present application discloses a skin audible watch for orientation identification. The watch includes a dial (1) and a strap (2). A plurality of sound collection modules (3) are arranged along a circumference of the dial (1), and the sound collection modules (3) are sequentially connected with a digital filter (4), an analog-to-digital converter (5), a single-chip microcomputer (6), and a row and column drive module (7); the single-chip microcomputer (6) is also connected with vibration motors (8) and a gyroscope (9); a number of the vibration motors (8) corresponds to a number of orientations; the digital filter (4), analog-to-digital converter (5), single-chip microcomputer (6), row and column drive module (7), the vibration motors (8) and the gyroscope (9) are located inside the dial (1); the row and column drive module (7) is connected with a current contact pin (12), and a free end of the current contact pin (12) extends out of a surface of the vibration motors (8).

In another embodiment, the watch includes a fixed shaft (10), the fixed shaft (10) being connected to the vibration motors (8) through an elastic connection piece.

In another embodiment, the row and column drive module (7) includes a row drive module (701) and a column drive module (702); the row drive module (701) includes a chip (7011), the chip (7011) is connected with a PNP transistor (7012), and address access lines A, B, C, and D of the PNP transistor (7012) are connected to P1.0, P1.1, P1.2, and P1.3 interfaces of the single-chip microcomputer (6); the column drive module (702) includes a first column drive module (7021) and a second column drive module (7022), 11th pin of the first column drive module (7021) is connected to P3.1 interface of the single-chip microcomputer (6), 14th pin of the first column drive module (7021) is connected to P3.0 interface of the single-chip microcomputer (6), No. 9 pin of the drive module (7021) is connected to No. 14 pin of the second column drive module (7022), and No. 9 pin of the second column of drive module (7022) is left floating, 13th pin of the first column drive module (7021) and 13th pin of the second column drive module (7022) are both grounded, and 10th pin of the first column drive module (7021) and 10th the second column drive module (7022) are connected to P1.5 interface of the single-chip microcomputer (6).

In another embodiment, the plurality of sound collection modules (3) are four sound collection modules (3), and four sound collection modules (3) are located on the dial (1) in four directions.

In another embodiment, the present application discloses an orientation recognition method based on a skin audible watch. The method includes the following steps:

Step 1: a plurality of sound collection module (3) collect sound signals from different directions, the sound signals are passed through a digital filter (4) to filter out high-frequency sound waves and to convert electric currents, and then an analog-to-digital converter (5) converts the electric currents to digital signals, the digital signals are saved into a single-chip microcomputer (6) for storage;

Step 2: the single-chip microcomputer (6) transmits the digital signals to a row and column drive module (7), and the row and column drive module (7) correspondingly drives a current contact pin (12) to generate a current to stimulate skin; and Step 3: the single-chip microcomputer (6) transmits the digital signals to a gyroscope (9), and the gyroscope (9) determines an attitude of the watch, points to an initial position of the sound signals according to the strength of the electric currents transmitted by each position, and feedbacks an azimuth signal to the single-chip microcomputer (6) to control a vibration of vibration motors (8) corresponding to the azimuth signal.

The beneficial effects of the present invention are:

The present invention discloses a skin audible watch for position recognition. A current contact pin is used for pre-remind, and then vibration motors are used for position reminder, so that the patient can accurately receive the sound source position. It does not cause any side effects, and is suitable for long-term use by hearing impaired people. It has a small size and is convenient to carry. The present invention discloses a method for position recognition of a skin audible watch for position recognition. Through the conversion between sound and electrical signal, it causes the human skin to perceive the vibration signal and helps the hearing impaired to distinguish the locations of the sound source.

In the figures: 1. Dial, 2. Strap, 3. Sound acquisition module, 4. Digital filter, 5. Analog-to-digital converter, 6. Single-chip microcomputer, 7. Row and column drive module, 701. Row drive module, 7011. Chip, 7012. PNP transistor, 702. Column drive module, 7021. First column drive module, 7022. Second column drive module, 8. Vibration motor, 9. Gyroscope, 10. Fixed shaft, 11. Cooling hole, 12. Current contact pin, 13. Split shaft, 14. Signal line, and 15. Elastic connector.

DETAILED DESCRIPTION

The present invention will be described in detail below with reference to the drawings and specific embodiments.

Figure 1:
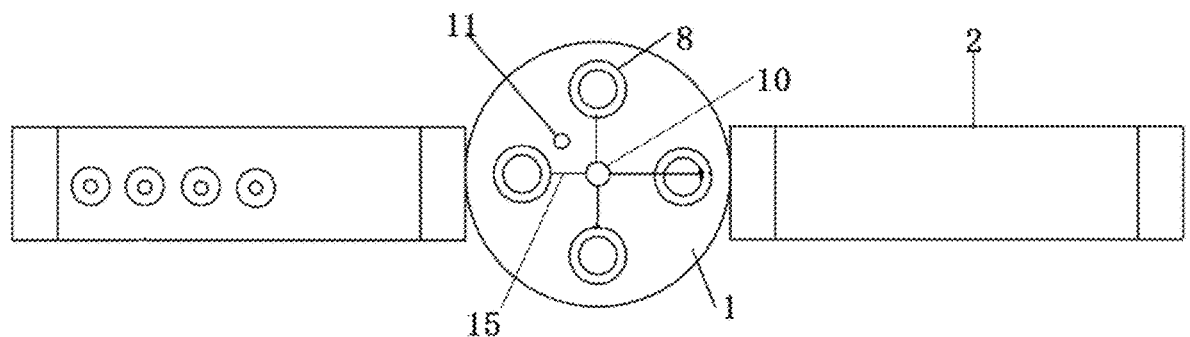
FIG. 1 is a schematic diagram of the structure of a skin audible watch for position recognition according to the present invention.
Figure 2:
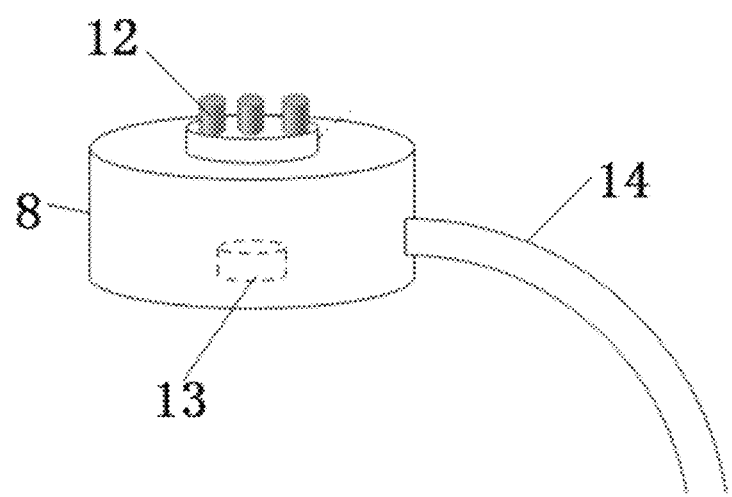
FIG. 2 is a schematic diagram of the structure of a vibration motor in a skin audible watch for position recognition according to the present invention.
Figure 3:
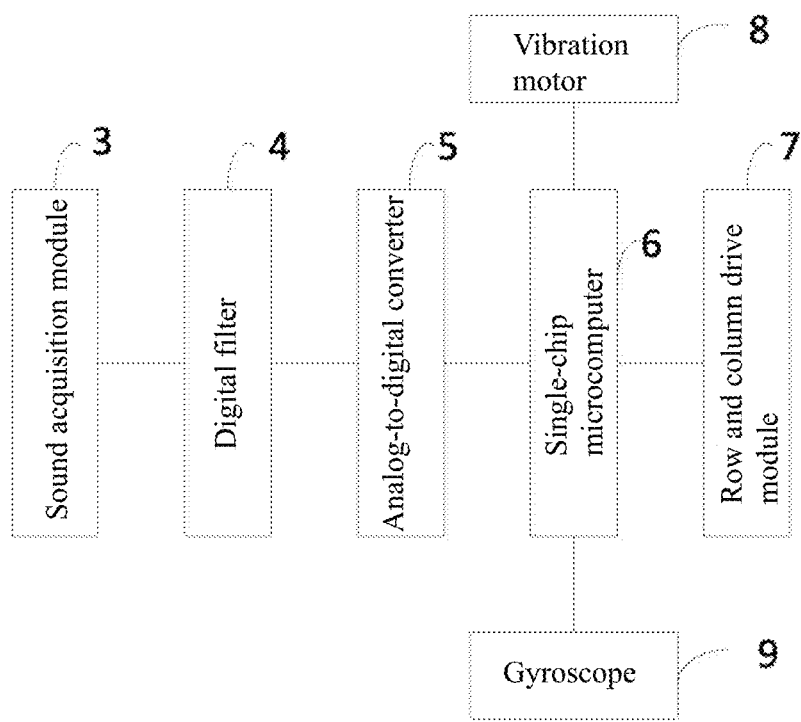
FIG. 3 is a schematic diagram of a skin audible watch for position recognition of the present invention.

A skin audible watch for position recognition, as shown in FIGS. 1, 2, and 3, includes a dial 1 and a strap 2. A plurality of sound collection modules 3 are arranged along a circumference of the dial 1. The sound collection modules 3 are sequentially connected with a digital filter 4, an analog-to-digital converter 5, a single-chip microcomputer 6, and a row and column drive module 7. The single-chip microcomputer 6 is also connected with vibration motors 8 and a gyroscope 9. There are four vibration motors 8 (front, back, left and right, four directions). The digital filter 4, the analog-to-digital converter 5, the single-chip microcomputer 6, the row and column drive module 7, the vibration motors 8, and gyroscope 9 are located inside the dial 1. The row and column drive module 7 is connected with a current contact pins 12. One end of the current contact pin 12 is inside the dial 1 and is electrically connected to the row and column drive module 7. The other end of the current contact pin 12 is connected to the surface of the vibration motors 8. The vibration motors 8 are connected to the single-chip microcomputer 6 via a signal line 14.

Figure 4:
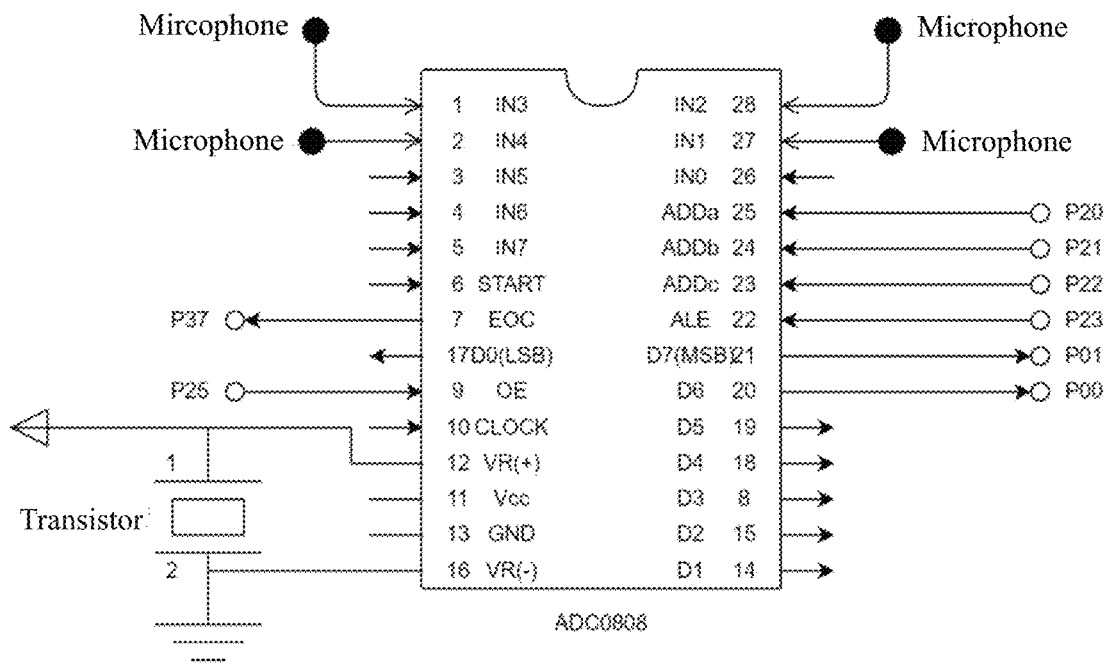
FIG. 4 is a schematic diagram of the structure of a row and column drive module in a skin audible watch for position recognition according to the present invention.

In some embodiments, the model of the single-chip microcomputer is AT89C52, and the structure of the analog-to-digital converter 5 is shown in FIG. 4. The sound collection modules 3 are silicon microphones SMA120, and there are four sound collection modules 3. The four sound collection modules 3 are located in the four directions of the dial 1. According to the Nyquist sampling theorem (Fs>2*Fn, where Fs is the sampling Rate, Fn is the signal frequency) to sample the audio.

The watch also includes a fixed shaft 10. Each vibration motor 8 is provided with a sub-shaft 13 at a center position, and the fixed shaft 10 is connected to the sub-shaft 13 through an elastic connecting member 15. The elastic connecting member may be a spring. A heat dissipation hole 11 is also provided on the back of the dial 1.

Figure 5:
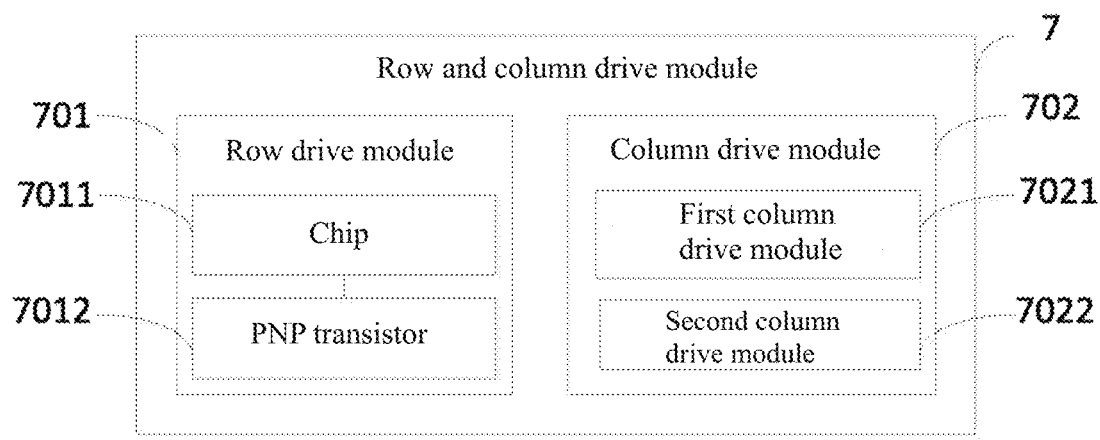
FIG. 5 is a schematic diagram of a row and column drive module in a skin audible watch for position recognition according to the present invention.
Figure 6:
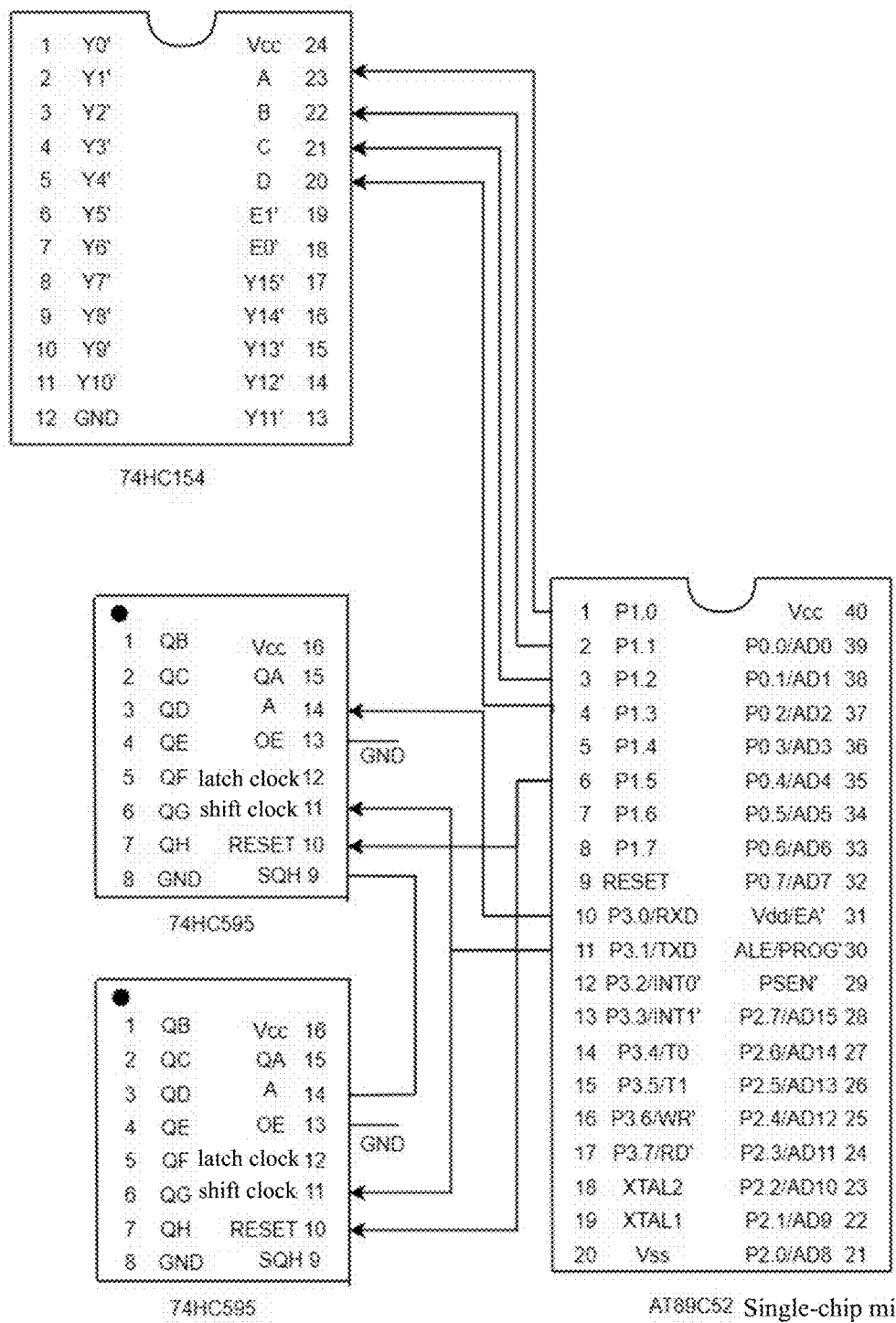
FIG. 6 is a schematic diagram of the connection between the PNP and the row driving module in a skin audible watch for position recognition according to the present invention.
Figure 7:
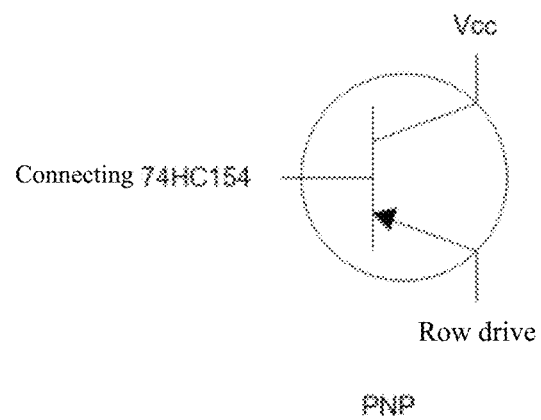
FIG. 7 is a schematic diagram of the structure of an analog-to-digital converter in a skin audible watch for position recognition according to the present invention.

As shown in FIGS. 5, 6, and 7, the row and column drive module 7 includes a row drive module 701 and a column drive module 702. The row drive module 701 includes a 74HC154 chip 7011. The chip 7011 is connected with a PNP transistor 7012. The address access lines A, B, C, and D of the PNP transistor 7012 B are connected to the P1.0, P1.1, P1.2, P1.3 interfaces of the microcomputer 6, respectively. The column drive module 702 includes a first column drive module 7021 and a second column drive module 7022. The first column drive module 7021 and the second column drive module 7022 are both 74HC595 chips. 11th pin of the first column drive module (7021) is connected to P3.1 interface of the single-chip microcomputer (6), 14th pin of the first column drive module (7021) is connected to P3.0 interface of the single-chip microcomputer (6), No. 9 pin of the drive module (7021) is connected to No. 14 pin of the second column drive module (7022), and No. 9 pin of the second column of drive module (7022) is left floating, 13th pin of the first column drive module (7021) and 13th pin of the second column drive module (7022) are both grounded, and 10th pin of the first column drive module (7021) and 10th the second column drive module (7022) are connected to P1.5 interface of the single-chip microcomputer (6).

An orientation recognition method for a skin audible watch based on orientation recognition, adopts the above-mentioned skin audible watch for orientation recognition, and includes the following steps:

Step 1. The sound collection modules 3 collect sound signals in different directions. The sound signals are passed through a digital filter 4 in the form of current signals to filter out high-frequency sound waves, adjusting the sound signals to a frequency suitable for human skin perception. The current signal is converted by an analog-to-digital converter 5 into a binary digital signal that is easy to be recognized by the computer and stored in the single-chip microcomputer 6. At the same time, the single-chip microcomputer 6 judges the htrsounds of different frequencies through fast Fourier transform $$\left(X_k = \sum_{n=0}^{N-1} x_n e^{-\frac{2\pi i}{N}kn} k = 0, 1, 2 \ldots N-1\right)$$

and active noise reduction technology, and obtains a sound category.

Figure 8:
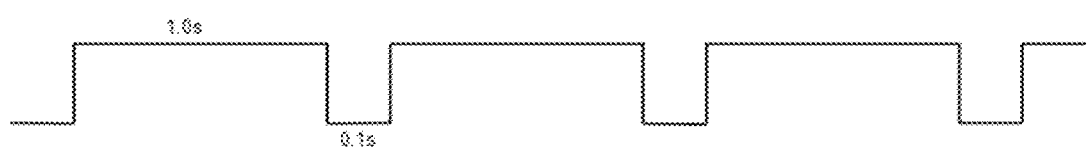
FIG. 8 is a schematic diagram of stimulating signal generation in a skin audible watch for position recognition of the present invention.

Step 2. The single chip microcomputer 6 transmits the signal to the row and column drive module 7. The row and column drive module 7 correspondingly drives the 16 rows and 16 columns of the current contact pin 12 to generate current to stimulate the skin. The stimulation frequency is realized every 0.1 seconds according to the pre-written algorithm. A current is generated, which disappears after 1s each time the current is excited, and is excited again after an interval of 0.1s, as shown in FIG. 8.

Step 3. The single-chip microcomputer 6 transmits the signal to the gyroscope 9, and the gyroscope 9 determines the attitude of the watch. According to the strength of the electric signal transmitted by each direction (the model of the gyroscope 9 is WTGAHRS2), the gyroscope points to the initial approximate position of the sound source, and feedbacks an azimuth signal to the single chip microcomputer 6 to control the vibration of the vibration motors 8 corresponding to the azimuth signal. For example, when the azimuth signal of the gyroscope 9 points the sound source to the front left, the azimuth signal is fed back to the single chip microcomputer 6, and the microcomputer 6 instructs the vibration motors 8 generate vibrations of different frequencies and amplitudes according to the sound type and controls the left and front vibration motors 8 to vibrate and thus allows users to perceive different sounds.

Further, in step 4, the single-chip microcomputer 6 reconstructs the main sound source according to the watch attitude and the sound signal collected by the sound collection module 3, and obtains the current slope of the main sound source in each direction. By comparing the current slopes on the left and the front, then the microcomputer increases the vibration frequency of the vibration motor 8 with a larger current slope.

Through the above method, the skin audible watch for position recognition of the present invention uses a current contact pin to give advance reminders and then vibration motors for position reminders, so that the patient can accurately receive the sound source position. The watch does not cause any side effects, and is suitable for hearing impaired people using for a long time. The watch is small in size and convenient to carry. The present invention also discloses a method for position recognition of a skin audible watch for position recognition. Through the conversion between sound and electrical signals, it causes the human skin to perceive vibration signals and helps the hearing impaired people to distinguish the locations of the sound source.

The invention claimed is:

1. A skin audible watch for orientation identification, comprising a dial (1) and a strap (2), wherein a plurality of sound collection modules (3) are arranged along a circumference of the dial (1), and the sound collection modules (3) are sequentially connected with a digital filter (4), an analog-to-digital converter (5), a single-chip microcomputer (6), and a row and column drive module (7); the single-chip microcomputer (6) is also connected with vibration motors (8) and a gyroscope (9); a number of the vibration motors (8) corresponds to a number of orientations; the digital filter (4), analog-to-digital converter (5), single-chip microcomputer (6), row and column drive module (7), the vibration motors (8) and the gyroscope (9) are located inside the dial (1); the row and column drive module (7) is connected with a current contact pin (12), and a free end of the current contact pin (12) extends out of a surface of the vibration motors (8).

2. The skin audible watch according to claim 1, further comprising a fixed shaft (10), the fixed shaft (10) being connected to the vibration motors (8) through an elastic connection piece.

3. The skin audible watch according to claim 1, wherein the row and column drive module (7) comprises a row drive module (701) and a column drive module (702); the row drive module (701) comprises a chip (7011), the chip (7011) is connected with a PNP transistor (7012), and address access lines A, B, C, and D of the PNP transistor (7012) are connected to P1.0, P1.1, P1.2, and P1.3 interfaces of the single-chip microcomputer (6); the column drive module (702) comprises a first column drive module (7021) and a second column drive module (7022), 11th pin of the first column drive module (7021) is connected to P3.1 interface of the single-chip microcomputer (6), 14th pin of the first column drive module (7021) is connected to P3.0 interface of the single-chip microcomputer (6), No. 9 pin of the drive module (7021) is connected to No. 14 pin of the second column drive module (7022), and No. 9 pin of the second column of drive module (7022) is left floating, 13th pin of the first column drive module (7021) and 13th pin of the second column drive module (7022) are both grounded, and 10th pin of the first column drive module (7021) and 10th the second column drive module (7022) are connected to P1.5 interface of the single-chip microcomputer (6).

4. The skin audible watch according to claim 1, wherein the plurality of sound collection modules (3) are four sound collection modules (3), and four sound collection modules (3) are located on the dial (1) in four directions.

5. An orientation recognition method based on a skin audible watch comprising the following steps:
   step 1: collecting by a plurality of sound collection module (3) sound signals from different directions, passing the sound signals through a digital filter (4) to filter out high-frequency sound waves, converting the filtered sound signals to electric currents, converting by an analog-to-digital converter (5) the electric currents to digital signals, and saving the digital signals into a single-chip microcomputer (6) for storage;
   step 2: transmitting by the single-chip microcomputer (6) the digital signals to a row and column drive module (7), and correspondingly driving by the row and column drive module (7) a current contact pin (12) to generate a current to stimulate skin; and
   step 3: transmitting by the single-chip microcomputer (6) the digital signals to a gyroscope (9), and determining by the gyroscope (9) an attitude of the watch, pointing points to an initial position of the sound signals according to the strength of the electric currents transmitted by each position, and feeding back an azimuth signal to the single-chip microcomputer (6) to control a vibration of vibration motors (8) corresponding to the azimuth signal.

* * * * *